United States Patent [19]

Simon et al.

[11] Patent Number: 5,762,907
[45] Date of Patent: *Jun. 9, 1998

[54] FROZEN RADIOPHARMACEUTICAL FORMULATIONS

[75] Inventors: Jaime Simon, Angleton; Joseph R. Garlich; R. Keith Frank, both of Lake Jackson; Kenneth McMillan, Richwood, all of Tex.

[73] Assignee: The Dow Chemical Company, Midland, Mich.

[*] Notice: The portion of the term of this patent subsequent to Nov. 21, 2006, has been disclaimed.

[21] Appl. No.: 133,806

[22] Filed: Oct. 7, 1993

Related U.S. Application Data

[63] Continuation of Ser. No. 538,871, Jun. 18, 1990, abandoned.

[51] Int. Cl.$^6$ .................. A61K 51/04; C09K 11/00
[52] U.S. Cl. ............... 424/1.77; 424/1.11; 424/1.53; 424/1.65; 534/10; 252/644; 252/645
[58] Field of Search ..................... 424/1.65, 1.11, 424/1.53, 1.77; 252/644, 645

[56] References Cited

U.S. PATENT DOCUMENTS

| | | | |
|---|---|---|---|
| 4,018,883 | 4/1977 | Parslow | 424/1.1 |
| 4,111,656 | 9/1978 | Margherita | 424/1.1 X |
| 4,301,140 | 11/1981 | Frank et al. | 424/1.1 |
| 4,341,755 | 7/1982 | Lindall | 424/1.1 |
| 4,411,881 | 10/1983 | Tzodikov | 424/1.1 |
| 4,457,602 | 7/1984 | Mizokami | 354/416 |
| 4,752,464 | 6/1988 | Lieberman et al. | 424/1.1 |
| 4,793,987 | 12/1988 | Henderson et al. | 424/1.1 |
| 4,853,209 | 8/1989 | Kaplan et al. | 424/1.1 |
| 4,898,724 | 2/1990 | Simon et al. | 424/1.1 |
| 4,937,333 | 6/1990 | Garlich et al. | 540/474 |
| 5,064,633 | 11/1991 | Simon et al. | 424/1.1 |
| 5,219,556 | 6/1993 | Wolfgangel | 424/1.1 |

FOREIGN PATENT DOCUMENTS

| | | |
|---|---|---|
| 0164843 | 4/1985 | European Pat. Off. . |
| 0164843 | 12/1985 | European Pat. Off. ....... A61K 43/00 |
| 0291605 | 10/1987 | European Pat. Off. . |
| 0291605 | 11/1988 | European Pat. Off. ....... A61K 43/00 |
| 0374501 | 11/1989 | European Pat. Off. . |
| 375376 | 12/1989 | European Pat. Off. . |
| 0374501 | 6/1990 | European Pat. Off. ....... A61K 43/00 |
| 0375376 | 6/1990 | European Pat. Off. ....... A61K 43/00 |
| 8900052 | 1/1989 | WIPO ........................ A61K 49/00 |
| 9006776 | 6/1990 | WIPO . |

OTHER PUBLICATIONS

*Physical Chemistry*, 4th Edition, Walter J. Moore (Prentice Hall, Englewood Cliffs, NJ) 1972, pp. 362–366, and 397–401.

*Medline Database*, abstr. 80062521, Bethesda, MD, US; M.H. McBride et al.: "Deterioration of stannous ion in radiopharmaceutical kits during storage" & Am. J. Hosp. Pharm. 1979, 36(10), 1370–1372.

*Medline Database*, abstr. 88066859, Bethesda, MD, US; A.P. Richardson et al.: "Optimization and batch productionof DTPA–labelled antibody kits for routine use in 111 IN immunoscintigraphy" & Nucl. Med. Commun. 1987, 8(5), 347–356.

Chem. Abstract 94(8):52884b (1980).
Bochkarev et al., *Khim. Farm Zh.* 14(10) 82–4 (Russ.).
Radioisotopes, 26(7), 451–457, (1977), H. Ikebuchi et al (abstract attached).
J. Pharm. Sci., 74(2), 197–200 (1985), B.J. Floor et al.
J. Pharm. Sci., 71(11), 1219–1223, (1982), A. Rego et al.
Chem. Abstracts 94(8), 52884b (1980).
Medline Database, abstract 80062521, Bethesda, MD, US; M.H. McBride et al., 1979.
Medline Database, abstract 88066859, Bethesda, MD, US; A.P. Richardson et al., 1987.

*Primary Examiner*—John Kight
*Assistant Examiner*—Lara C. Kelley
*Attorney, Agent, or Firm*—Karen L. Kimble

[57] ABSTRACT

Radiopharmaceutical formulations for complexes comprising at least one radionuclide complexed with a ligand, or its physiologically-acceptable salts thereof, especially $^{153}$samarium-ethylenediaminetetramethylenephosphonic acid, which optionally contains a divalent metal ion, e.g. calcium, and is frozen, thawed, and then administered by injection.

38 Claims, 2 Drawing Sheets

FROZEN RADIOPHARMACEUTICAL FORMULATIONS

CROSS REFERENCE

The present application is a continuation application from U.S. Ser. No. 538,871, filed Jun. 18, 1990, now abandoned.

FIELD OF THE INVENTION

The present invention relates to formulations for radiopharmaceuticals.

BACKGROUND OF THE INVENTION

The development of bone metastasis is a common and often catastrophic event for a cancer patient. The pain, pathological fractures, frequent neurological deficits and forced immobility caused by these metastatic bone lesions significantly decrease the quality of life for the cancer patient. The number of patients that contract metastatic disease is large since nearly 50% of all patients who contract breast, lung or prostate carcinoma will eventually develop bone metastasis. Bone metastasis are also seen in patients with carcinoma of the kidney, thyroid, bladder, cervix, and other tumors, but collectively, these represent less than 20% of patients who develop bone metastasis. Metastatic bone cancer is rarely life threatening and occasionally patients live for years following the discovery of the bone lesions. Initially, treatment goals center on relieving pain, thus reducing requirements for narcotic medication and increasing ambulation. Clearly, it is hoped that some of the cancers can be cured.

Radiopharmaceuticals used in the formulations of the present invention have been prepared as their metal-ligand complexes, particularly $^{153}$Sm-EDTMP, in U.S. Pat. No. 4,898,724, the disclosure of which is hereby incorporated by reference. The $^{153}$Sm-EDTMP, especially as its pharmaceutical formulation, has a utility for the relief of bone pain and for the treatment of calcific tumors, which utility and preparation has been given in U.S. Pat. No. 4,898,724, U.S. application Ser. No. 457,602, filed Dec. 27, 1989, now abandoned, U.S. application Ser. No. 452,848, filed Dec. 19, 1989, now U.S. Pat. No. 5,064,633, and U.S. application Ser. No. 284,876, filed Dec. 19, 1988, now U.S. Pat. No. 5,059,412, the disclosures of which are hereby incorporated by reference. The additional use of radiopharmaceuticals for bone marrow suppression is given in U.S. Pat. No. 4,853,209, the disclosure of which is hereby incorporated by reference. All of these references disclose a use of the radiopharmaceuticals of the present invention, particularly $^{153}$Sm-EDTMP, in a formulation with suitable pharmaceutically-acceptable carriers.

One concern when administering any radiopharmaceutical is the potential for radiolytic degradation of the organic(s) molecules present in the formulation which may alter the biodistribution of the radioisotope or result in toxic by-products. Neither of these events is desirable. When high amounts of radioactivity are needed, there is the increased potential for radiation damage to the organic molecule (e.g. EDTMP). This degradation is more likely to occur when therapeutic radionuclides (e.g. $^{153}$Sm) are used which are designed to deliver high radiation doses.

One approach that has been tried to prevent radiolysis is to add a free radical inhibitor to the formulation. However, the inhibitor or its degradation products may be toxic or interfere with the biodistribution of the radiopharmaceutical. Use of an inhibitor such as benzyl alcohol is discussed by H. Ikebuchi et al., *Radioisotopes* 26(7), 451–7 (1977); B. J. Floor et al., *J. Pharm. Sci.* 74(2), 197–200 (1985); and A. Rego et al., *J. Pharm. Sci.* 71(11), 1219–23 (1982).

A further concern for radiopharmaceutical formulations (as shown in U.S. Pat. No. 4,898,724 and U.S. application Ser. No. 457,602, now abandoned) is that a molar excess of ligand (e.g. EDTMP) compared with the amount of metal may be used. When large amounts of metal ions (e.g. Sm$^{+3}$) are injected, a much larger amount of free chelating agent (e.g. EDTMP) is therefore also injected. The excess ligand present may be able to complex metal ions in the bloodstream which may lead to complications for the patient. It is therefore desirable to have a formulation that contains a minimal amount of free chelating agent.

Another concern when administering radiopharmaceuticals is the mode of injection. Typically, all such radiopharmaceuticals are administered by intravenous injections (I.V.). The patient can experience some discomfort with an I.V. injection and sometimes it is difficult to find a suitable vein available in the patient.

Consequently, it would be advantageous to have a formulation for radiopharmaceuticals which had minimal radiolysis prior to use, could be injected by several routes, and avoided excess free (or uncomplexed) ligand.

SUMMARY OF THE INVENTION

Surprisingly, an improved formulation for administering radiopharmaceuticals, especially $^{153}$Sm-EDTMP, has now been found which reduces radiolysis of the EDTMP without altering the performance of the radiopharmaceutical. Radiopharmaceuticals suitable for use in the present formulations of this invention include complexes comprising at least one radionuclide complexed with a ligand or a physiologically-acceptable salt thereof.

Examples of suitable radionuclides are Samarium-153 ($^{153}$Sm), Holmium-166 ($^{166}$Ho), Ytterbium-175 ($^{175}$Yb), Lutetium-177 ($^{177}$Lu), Yttrium-90 ($^{90}$Y) or Gadolinium-159 ($^{159}$Gd). Especially preferred radionuclides are $^{153}$Sm and $^{166}$Ho, with $^{153}$Sm being most preferred.

Examples of suitable ligands are ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), tris(2-aminoethyl)aminehexamethylenephosphonic acid (TTHMP), 1-carboxyethylenediaminetetramethylenephosphonic acid (CEDTMP), bis(aminoethylpiperazine)tetramethylenephosphonic acid (AEPTMP), and 1,4,7,10-tetraazacyclododecanetetramethylenephosphonic acid (DOTMP), and physiologically-acceptable salts thereof. Particularly preferred ligands are EDTMP, DTPMP, HEEDTMP, TTHMP, AEPTMP, CEDTMP and DOTMP, with EDTMP being particularly preferred. A particularly preferred radiopharmaceutical for use in the present invention is $^{153}$Sm-EDTMP and its physiologically-acceptable salts.

The present formulations can also contain a divalent metal ion of from about 0.25 to about 5 moles of divalent metal ion per mole of ligand which does not interfere with the formation of the radiopharmaceutical complex.

Also, it has now been found that I.V. injection is not required to obtain the desired biodistribution of radionuclide when using a radiopharmaceutical formulation of the present invention. Rather, when desired or necessary, I.P., S.C. or I.M. injections provide similar biodistributions.

DETAILED DESCRIPTION OF THE INVENTION

The present radiopharmaceutical formulations which contain the divalent metal minimize the presence of free (or uncomplexed) ligand (e.g., EDTMP) to be introduced into the bloodstream of the mammal. This divalent metal-ligand complex reduces the chelation of other metals (e.g., calcium) in the blood by the ligand. Thus, the deleterious effect of the excess ligand is decreased. However, the divalent metals must not interfere with the formation of the radiopharmaceutical complex (e.g., $^{153}$Sm-EDTMP). Suitable divalent metals are $Fe^{+2}$ and $Mn^{+2}$ and the alkaline earths, for example, $Mg^{+2}$, $Ca^{+2}$, $Sr^{+2}$ and $Ba^{+2}$, with $Ca^{+2}$ being most preferred. These radiopharmaceutical formulations are prepared such that from about 0.25 to about 5 moles of the divalent metal is present per mole of ligand, especially preferred from about 0.5 to about 3 moles, preferably from about 0.5 to about 1 mole, more preferably from about 0.75 to about 1 mole, and most preferably from about 0.9 to about 1 mole.

There are several ways to prepare such divalent metal radiopharmaceutical formulations. One way (Method A) is by preparing a divalent metal formulation which is added to the radioactive metal-ligand complex. The radioactive metal-ligand complex may optionally have been frozen, then thawed to add the divalent metal and could, if desired, be refrozen and then thawed prior to use. A second way (Method B) is by adding the divalent metal to the radioactive metal ion solution. The ligand is then added to form the complex and then this formulation is frozen, if desired. Because radiolysis does not occur until the ligand is added, freezing is used if the time lapse prior to use makes that desirable. The third way, is to coadminister the radiopharmaceutical, which may have been frozen and thawed for use, with a divalent metal ion solution, e.g., calcium gluconate, by two separate I.V. injections at about the same time to the patient. The fourth way, and the preferred way (Method D) is to add the divalent metal, as its chloride or more preferably as its hydroxide, to the ligand and then adjust the pH, e.g., by adding NaOH, optionally freeze-drying the solution to form a divalent metal-ligand lyophilized formulation (kit). The acidic solution of radioactive metal ion is used to reconstitute the kit and results in the radiopharmaceutical formulation suitable for use and at the desired pH. One concern in any of the methods to form the radiopharmaceutical formulation is the half-life of the radionuclide being used (e.g., $^{153}$Sm $t_{1/2}$=about 46 hrs.). Another concern is the length of time that the radionuclide is in solution with the ligand. The amount of activity and the time the radionuclide is in solution with the ligand will determine the desirability of freezing the radiopharmaceutical formulation.

Kits were prepared containing a ligand formulation of about one equivalent of divalent metal per equivalent of ligand in the preferred embodiment (Method D). Also the divalent metal-ligand solution can be freeze-dried, which, when reconstituted with a solution of radionuclide, forms a quantitative complex with the radioactive metal ion and has a pH of from about 7 to about 8.5. The divalent metal formulation is especially preferred when large doses of ligand are used, usually with the higher doses of radionuclide, especially used for bone marrow ablation.

Thus, preferably the kits containing the ligand, such as EDTMP, optionally with the divalent metal present, are freeze-dried in such a manner that the addition of a predetermined amount of radionuclide solution in a suitable concentration of HCl (preferably from about 0.001 to 1N HCl, or more preferably from about 0.01 to about 0.1N HCl) which would result in a quantitative yield of radionuclide-ligand complex, e.g., Sm-EDTMP, and have a resulting pH of between 7 to 8.5. For the radiopharmaceutical formulation $^{153}$Sm-EDTMP, the preferred concentration of EDTMP is 35 mg/mL and the preferred Sm concentration is $3\times10^{-4}$M (i.e. about 278:1 EDTMP:Sm).

The present radiopharmaceutical formulations, especially $^{153}$Sm-EDTMP formulations, with or without the divalent metal present, can be frozen to minimize radiolysis of the ligand, then thawed prior to use. The freezing can be done by any convenient means which maintains the sterility of the product (e.g., by liquid nitrogen or dry ice), then when it is desired to use the formulation, it is allowed to thaw.

The route of administration of the present formulations may be selected from I.V., I.P., S.C. or I.M. The biodistribution results are similar for the present radiopharmaceutical formulations by all the injection routes.

An improved method for preparing radiopharmaceuticals, especially $^{153}$Sm-EDTMP, has now been found which reduces radiolysis of the ligand without altering the performance of the radiopharmaceutical. Radiopharmaceuticals suitable for use in the present formulations of this invention include complexes comprising at least one radionuclide complexed with a ligand, or physiologically-acceptable salts thereof.

Examples of suitable radionuclides are Samarium-153 ($^{153}$Sm), Holmium-166 ($^{166}$Ho), Ytterbium-175 ($^{175}$Yb), Lutetium-177 ($^{177}$Lu), Yttrium-90 ($^{90}$Y) or Gadolinium-159 ($^{159}$Gd). Especially preferred radionuclides are $^{153}$Sm and $^{166}$Ho, with $^{153}$Sm being most preferred.

Examples of suitable ligands are ethylenediaminetetramethylenephosphonic acid (EDTMP), diethylenetriaminepentamethylenephosphonic acid (DTPMP), hydroxyethylethylenediaminetrimethylenephosphonic acid (HEEDTMP), nitrilotrimethylenephosphonic acid (NTMP), tris(2-aminoethyl)aminehexamethylenephosphonic acid (TTHMP), 1-carboxyethylenediaminetetramethylenephosphonic acid (CEDTMP), bis(aminoethylpiperazine) tetramethylenephosphonic acid (AEPTMP), and 1,4,7,10-teraazacyclododecanetetramethylenephosphonic acid (DOTMP), and physiologically-acceptable salts thereof. Particularly preferred ligands are EDTMP, DTPMP, HEEDTMP, TTHMP, AEPTMP, CEDTMP and DOTMP, with EDTMP being particularly preferred. A particularly preferred radiopharmaceutical for use in the present invention is $^{153}$Sm-EDTMP and its physiologically-acceptable salts. Suitable physiologically-acceptable salts have been defined in U.S. Pat. No. 4,898,724, which disclosure is hereby incorporated by reference.

DEFINITIONS

Sm=samarium, all isotopes both radioactive and not. (Similarly for the other radionuclides of the invention.)

$^{153}$Sm=is the radioactive isotope of samarium having an atomic mass of 153. (Similarly for the other radionuclides of the invention.)

EDTMP=ethylenediaminetetramethylenephosphonic acid.

$^{153}$Sm-EDTMP=$^{153}$samarium-ethylenediaminetetramethylenephosphonic acid, which is a complex in solution; it contains both radioactive and non-radioactive isotopes of samarium.

Spiked=1–2 μL of about 0.5 to about 1 picoCi $^{153}$SmCl$_3$ or $^{166}$HoCl$_3$ solution was added as a tracer.

Radiopharmaceutical=a radioactive pharmaceutical for diagnosis and/or therapy, usually a solution containing a radioactive metal ion (e.g., $^{153}$Sm) attached to an organic ligand (e.g., EDTMP) in an aqueous solution.

Kit=a vial containing a solid ligand formulation, optionally containing a divalent metal ion, to which a solution of radioactive metal ion is added for the purpose of forming the radioactive metal-ligand complex.

X-mL kit=a kit designed to receive X-mL of radioactive metal ion solution for the purpose of forming the radionuclide-ligand complex.

Reconstituted=addition of an acidic radionuclide solution to a kit for the purpose of forming a radionuclide-ligand complex.

TBA=tetrabutylammonium hydroxide
BzOH=benzyl alcohol
EtOH=ethanol
I.V.=intravenous injection
I.P.=intraperitoneal injection
I.M.=intramuscular injection
S.C.=subcutaneous injection
MDP=methylenediphosphonate

GENERAL EXPERIMENTAL

The cation exchange chromatographic separation method was used to determine the complex yield. This procedure is described in U.S. Pat. No. 4,898,724, the disclosure of which is hereby incorporated by reference.

HPLC=high performance liquid chromatography; the column used was a Hamilton™ PRP-1 reverse phase, the eluent was 0.1M sodium acetate and 0.005M TBA. The flow rate was 1 mL/min; detection was with a radiometric detector and U.V. detector (240 nm) coupled in series.

The EDTMP was prepared in a pure form, suitable for use as a pharmaceutical by the method described in U.S. application Ser. No. 389,441, filed Aug. 4, 1989, now U.S. Pat. No. 4,937,333, which disclosure is hereby incorporated by reference.

The $^{153}$Sm was obtained from the research reactor at the University of Missouri, Columbia, Mo.

Barnstead NANOpure™ water was used as the distilled water.

Ca(OH)$_2$ was as the dihydrate from MCB or Aldrich, 95% pure.

All reagents not otherwise specified were purchased and used as received.

The invention will be further clarified by a consideration of the following examples, which are intended to be purely exemplary of the present invention.

EXAMPLE 1

Method A, No Calcium Added

Three mL of a 8×10$^{-2}$M EDTMP solution was prepared that was 3×10$^{-4}$M in Sm. The specific activity was 100 mCi of $^{153}$Sm per mL. Three 200 μL aliquots (Samples I, II and III) were placed in plastic vials and frozen using a dry ice-acetone bath. The plastic vials were kept in a freezer. Another 500 μL portion was placed in a glass vial and 4.3 μL of benzyl alcohol were added to result in a 0.9% (wt/vol) solution (Sample A). A further 500 μL portion was placed in a glass vial and 31.8 μL of ethanol were added to result in 5% (wt/vol) solution (Sample B).

The solutions were analyzed by HPLC and degradation was monitored as a function of time. Degradation was evidence by the appearance of non-Sm-EDTMP peaks in the radiometric chromatogram. For this time study, one frozen plastic vial was allowed to thaw at ambient temperature and a portion was analyzed. The solution was allowed to stand without freezing for 2 to 4 hours and the analysis on the solution repeated. The other two plastic vials were used to get data at larger time intervals in a similar manner.

The results showed only one radiometric peak corresponding to the desired product for over a 60 hour period for the frozen samples. The control (non-inhibited sample) and both the benzyl alcohol and the ethanol samples showed several radiometric peaks. The percent radiation that did not correspond to the desired product as a function of time from reconstitution is shown in Table 1.

TABLE 1

INHIBITION OF RADIOLYTIC DEGRADATION (100 mCi/mL)

| Sample | Time (hours) | % Degradation |
|---|---|---|
| Control | 0.25 | 0 |
| Control | 1.17 | 0 |
| Control | 4.3 | 0.4 |
| Control | 6.3 | 0.9 |
| Control | 12.25 | 4.9 |
| Control | 24.0 | 18.3 |
| A | 10.2 | 0.1 |
| A | 25.5 | 2.6 |
| B | 9.2 | 0.5 |
| B | 26.2 | 18.2 |
| I | 8.25 | 0 |
| I | 10.9 | 0 |
| II | 22.6 | 0 |
| II | 27.0 | 0 |
| III | 48.2 | 0 |
| III | 70.5 | 0.1 |

A = 0.9% BzOH, comparative
B = 5% EtOH, comparative
I = frozen, thawed at 8.25 hrs. and analyzed, left thawed until 10.9 hrs. for analysis
II = frozen, thawed at 21 hrs., analyzed at 22.6 hrs. and at 27 hrs.
III = frozen, thawed at 48.2 hrs., analyzed, refrozen, then thawed again at 70.5 hrs. for analysis Samples A and B are not of the invention; Samples I, II and III are of the invention.

Figure 1:
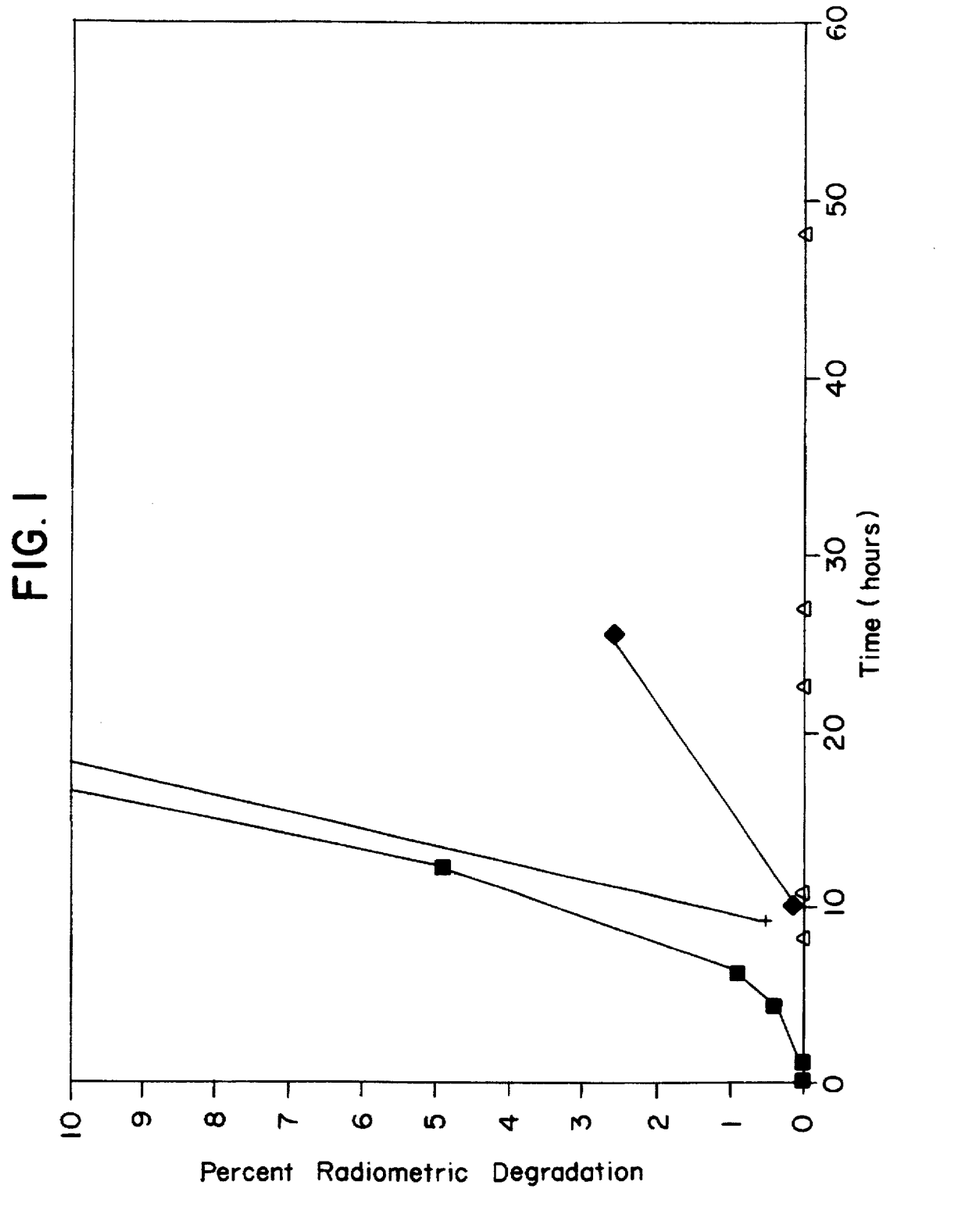
FIG. 1 shows the radiolysis of EDTMP with 100 mCi/mL specific activity of $^{153}$Sm in the presence of 5% EtOH, 0.9% BzOH, frozen and a control.

The results are also shown by FIG. 1.

Example A (Comparative; Control)

Samples were prepared by the procedure described in Example 1, except that the specific activity of $^{153}$Sm was 30, 30, and 50 mCi/mL (Samples C, D, and E, respectively). The results are given in Table A.

Figure 2:
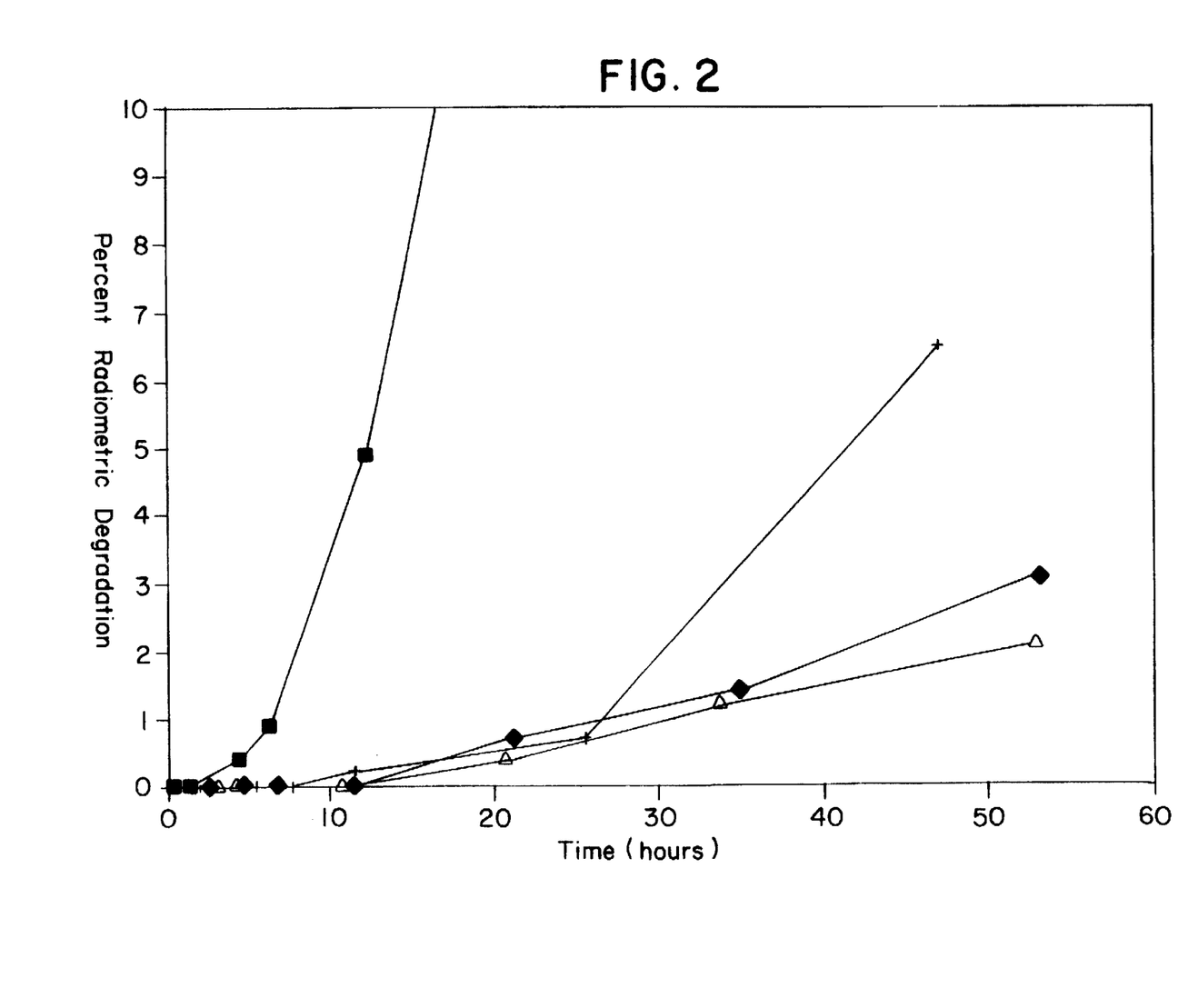
FIG. 2 shows the radiolysis of EDTMP at different specific activities of $^{153}$Sm.

These results, along with the control (100 mCi/mL) from Example 1 are shown graphically in FIG. 2. This graph demonstrates that the rate of radiolytic degradation is proportional to the specific activity of the radionuclide.

TABLE A

UNINHIBITION OF RADIOLYTIC DEGRADATION

| Sample | Time (hours) | % Degradation |
|---|---|---|
| C | 0.3 | 0 |
| C | 2.25 | 0 |
| C | 4.47 | 0 |
| C | 6.75 | 0 |
| C | 11.3 | 0 |
| C | 21.25 | 0.7 |
| C | 35.0 | 1.4 |
| C | 53.0 | 3.1 |
| D | 0.17 | 0 |
| D | 2.42 | 0 |
| D | 4.5 | 0 |
| D | 6.6 | 0 |
| D | 10.75 | 0 |
| D | 20.6 | 0.4 |
| D | 33.8 | 1.2 |
| D | 52.83 | 2.1 |
| E | 2.0 | 0 |
| E | 5.25 | 0 |
| E | 7.6 | 0 |
| E | 11.5 | 0.2 |
| E | 25.5 | 0.7 |
| E | 47.0 | 6.5 |

EXAMPLE 2

Method A, No Calcium Added

Two solutions were prepared as described in Example 1, except that they contained 27 mCi/mL of $^{153}$Sm and were frozen in the same manner as Example 1. The samples were stored in a container filled with powdered dry ice. Samples were taken after allowing the solution to thaw, and then the solution was refrozen. The HPLC procedure of Example 1 was used to analyze the samples. No radiometric peaks other than the one corresponding to the desired product were detected after being frozen for a period of 70 hours.

EXAMPLE 3

Method A

Three mL of 70 mg/mL of EDTMP solution were pipetted into a beaker. The pH of the solution was adjusted to about 10.26 with 50% (wt/wt) NaOH. After placing the solution in a serum vial, the water was removed in a vacuum oven. Three such vials were prepared ("EDTMP kits").

Three 6.0 mL EDTMP kits, made by the above procedure, were reconstituted with HoCl$_3$ at $3\times10^{-4}$M in 0.1N HCl. Each kit was spiked with 150 µL of $^{166}$Ho. The pH of the complex solution was measured for each sample and found to be from 7.6 to 7.7. To one sample (Sample IV) was added CaCl$_2$ to achieve a 1:1 molar ratio of Ca:EDTMP. To another sample (Sample V) was added CaCl$_2$ to achieve a 2:1 molar ratio of Ca:EDTMP. The third sample was the control (without CaCl$_2$ added). Sample IV, upon the addition of CaCl$_2$, had a pH of 7.06 which was then adjusted to a pH of 7.5 with 50% (wt/wt) NaOH. Sample V, upon the addition of CaCl$_2$, had a pH of 6.6 which was then adjusted to a pH of 7.5 with 50% (wt/wt) NaOH. The percent complexation was found to be 99% for all three samples.

Three groups of 3 Sprague-Dawley rats were each injected I.V. with 100 µL of the Control, Sample IV and Sample V. After two hours the biodistribution was determined and the results are shown in Table 2.

TABLE 2

| | % INJECTED DOSE ($^{166}$Ho) IN VARIOUS TISSUES | | |
|---|---|---|---|
| Tissue | Control[d] | Sample IV[d] (1:1) | Sample V[d] (2:1) |
| Skeleton[a] | 53 | 46 | 43 |
| Liver | 0.07 | 0.95 | 0.07 |
| Kidney | 0.60 | 0.30 | D.30 |
| Spleen | 0.01 | 0.01 | 0.01 |
| Muscle[b] | 0.34 | 0.311 | 0.43 |
| Blood[c] | 0.08 | 0.20 | 0.22 |

[a] was derived by multiplying the % in the femur by 25
[b] was estimated as 43% of body weight
[c] was estimated at 6.5% of body weight.
[d] was average of 3 rats The data indicates that the biodistribution is similar for all three samples.

EXAMPLE 4

Method D

A Ca containing-kit (Ca-kit) (1:1 mole Ca:EDTMP) was prepared by stirring the following reagents at pH=1.97:

TABLE 3

| Reagent | g | mmol | mL |
|---|---|---|---|
| water | — | — | 30 |
| EDTMP (96%) | 2.198 | 4.84 | — |
| Ca(OH)$_2$ (95%) | 0.3766 | 4.83 | — |

The pH was then adjusted with 0.1N NaOH. At pH=1.97 the solution was clear. At pH=2.8 to 3 the solution is cloudy. At pH=about 5.8 the solution was clear. At pH=about 10.5 the solution was clear.

The preferred method of preparing the Ca-kit was to weigh out the solid Ca(OH)$_2$ and EDTMP into a beaker; add water and stir until clear; adjust the pH above 6.

The pH can then be adjusted to 9.2 and freeze-dried to obtain the desired formulation in kit form. A addition of Sm solution to the kit forms the $^{153}$Sm-EDTMP complex which can then be injected.

EXAMPLE 5

Method D $^{153}$Sm-EDTMP formulation was prepared by reconstituting a 3 mL Ca-kit from Example 4 (1:1 mole Ca:EDTMP). The kit was reconstituted by using $3\times10^{-4}$M Sm in 0.1N HCl solution spiked with $^{153}$Sm and the pH was adjusted to 7.8 (Sample VI). A $^{153}$Sm-EDTMP formulation (2:1 Ca:EDTMP) was prepared by a modification of the procedure of Example 4. The kit was reconstituted by using $3\times10^{-4}$M Sm in 0.1N HCl solution spiked with $^{153}$Sm and the pH was adjusted to 7.2 (Sample VII). Also a 6 mL kit as control without Ca was reconstituted with 6.0 mL of $3\times10^{-4}$M Sm in 0.1N HCl solution spiked with $^{153}$Sm and adjusting the pH to 7.5. The percentage of Sm (all Sm isotopes) as a complex was determined by cation exchange chromatography to be >99%.

Three Sprague-Dawley rats were injected I.V. with 100 μL of $^{153}$Sm-EDTMP solution. The rats were killed 2 hours after injection. The amount of activity in several tissues was determined by comparing the counts in the tissue (measured using a NaI gamma counter) to counts in standard 100 μL volumes of the stock solution and Table 4 shows the results:

TABLE 4

% INJECTED DOSE (153Sm) IN VARIOUS TISSUES

| Tissue | Control[d] | Sample IV[d] (1:1) | Sample V[d] (2:1) |
|---|---|---|---|
| Skeleton[a] | 44 | 37 | 38 |
| Liver | 0.14 | 0.15 | 0.20 |
| Kidney | 0.36 | 0.148 | 0.48 |
| Spleen | 0.01 | 0.01 | 0.01 |
| Muscle[b] | 0.53 | 0.60 | 0.96 |
| Blood[c] | 0.21 | 0.37 | 0.51 |

[a]was derived by multiplying the % in the femur by 25
[b]was estimated as 43% of body weight
[c]was estimated at 6.5% of body weight.
[d]was average of 3 rats

EXAMPLE 6

Method D

A 3 mL Ca-kit, as prepared in Example 4, was reconstituted with 3.0 mL of $3 \times 10^{-4}$M SmCl$_3$ in 0.1M HCl. Two mL of the solution were checked for pH and found to be between 7.0 and 8.0 by colorpHast™ pH strip. The solution was spiked with 1–2 μL of $^{153}$Sm solution as a tracer. In a similar manner a control kit, with Na, (without Ca, prepared as in Example 3) was reconstituted. Also a Ca-kit reconstituted to contain 48.3 mCi/mL of $^{153}$Sm was frozen in dry ice. After 21 days the frozen formulation was thawed and used.

Five Sprague-Dawley rats were injected I.V. with 100 μL solution of the control formulation, five Sprague-Dawley rats were injected with 100 μL of the 21 day old freshly thawed Ca-kit formulation, and 4 Sprague-Dawley rats were injected with 100 μL solution of the Ca-kit formulation (with tracer $^{153}$Sm).

The rats were killed 2 hours after injection. The amount of activity in several tissues was determined by comparing the counts in the tissue (measured using a NaI gamma counter) to counts in standard 100 μL volumes of the stock solution. The dose in several tissues is shown in Table 5 below.

TABLE 5

% INJECTED DOSE (153Sm) IN VARIOUS TISSUES

| Tissue | Control[d] No Ca | 21 Day Old Frozen Ca-kit[d] | Fresh spiked Ca-kit[e] |
|---|---|---|---|
| Skeleton[a] | 53 | 50 | 50 |
| Liver | 0.24 | 0.21 | 0.21 |
| Kidney | 0.49 | 0.41 | 0.41 |
| Spleen | 0.01 | 0.01 | 0.01 |
| Muscle[b] | 1.18 | 0.92 | 0.92 |
| Blood[c] | 0.16 | 0.21 | 0.20 |

[a]was derived by multiplying the % in the femur by 25
[b]was estimated as 43% of body weight
[c]was estimated at 6.5% of body weight.
[d]average of 5 rats
[e]average of 4 rats

EXAMPLE 7

Method D

Into a 600 mL beaker containing a magnetic stir bar was added 18.210 g (40.126 mmol) of EDTMP, 2.678 g (36.140 mmol) of Ca(OH)$_2$, and 400 mL of water. The mixture was stirred for 1 hour at room temperature and most of the solids dissolved. The pH was slowly raised using a solution of 50% NaOH, and stirring continued until all the solids dissolved. Once the mixture became homogeneous, the pH was slowly raised to 9.2 using a solution of 50% NaOH. (The solution turned cloudy at pH 3.6 and became homogenous again at pH 5.8.) The solution was transferred to a 500 mL volumetric flask and was brought to 500 mL by addition of water; the pH was 9.17. The solution was then filtered through a 0.45 micron filter and dispensed into multiple 3, 6 and 18 mL kits. The kits were frozen using a dry ice-acetone bath and then placed into a freeze-dryer. After 4 days the kits were removed, sealed, evacuated, labeled and stored.

A 3 mL Ca-kit from above along with a control (Na) kit, were each reconstituted using 3 mL of $3 \times 10^{-4}$M Sm in 0.1M HCl spiked with tracer amounts of $^{153}$Sm (1 to 2 μL). The percent complex was determined by cation exchange chromatography and each was determined to be >99%. The pH of both was between 7 and 8. Three 100 μL aliquots from each kit were drawn to be used as standards.

Five Sprague-Dawley rats (150–200 g) were injected I. V. with 100 μL of the reconstituted Ca-kit and four Sprague-Dawley rats were injected with 100 μL of the reconstituted control kit. After a period of 2 hours the rats were sacrificed and tissue samples were taken. The tissue samples were counted along with the standards and the biodistribution was determined. The results are shown in Table 6.

TABLE 6

% INJECTED DOSE (153Sm) IN VARIOUS TISSUES

| Tissue | Ca-kit % Dose in[a] | Control Na Kit % Dose in[b] |
|---|---|---|
| Bone | 50 | 53 |
| Liver | 0.21 | 0.24 |
| Kidney | 0.41 | 0.49 |
| Spleen | 0.01 | 0.01 |
| Muscle | 0.92 | 1.18 |
| Blood | 0.02 | 0.16 |
| Urine[c] | 52 | 51 |

[a]average of 5 rats
[b]average of 4 rats
[c]found in paper in cage

The two formulations appear to give equivalent biodistributions.

EXAMPLE 8 AND COMPARATIVE EXAMPLE B

Method D

When a Ca-kit formulation was compared to a Na-kit formulation, with both formulations administered to Sprague-Dawley rats by rapid I.V. injection, the Ca-kit had an LD$_{50}$ of 3.5 times greater than for the Na-kit. Both kits were prepared by the procedure of Example 5. The biodistribution results of the kits were similar. Because of the increased LD$_{50}$, the Ca-kit provides an added safety factor.

EXAMPLE 9

Method D

A $^{153}$Sm-EDTMP formulation was prepared by reconstituting a 3 mL kit prepared by the procedure of Example 3.

The kit was reconstituted by adding 3 mL of $^{153}$Sm solution in 0.1M HCl. The reconstituted kit contained $3\times10^{-4}$M of Sm and 35 mg/mL of EDTMP.

The percentage of Sm as a complex was determined by cation exchange chromatography to be >99%. Two Sprague-Dawley rats were injected I.M. in the right thigh and two more rats were injected S.C. over the clavia at the neck. Each rat received 100 µL of $^{153}$Sm-EDTMP solution.

The rats were killed 2 hours after injection. The amount of activity in several tissues was determined by comparing the counts in the tissue (measured using a NaI gamma counter) to counts in standard 100 µL volumes of the stock solution. The dose in several tissues is shown in Table 7 below and compared to I.V. injections done similarly.

TABLE 7

% INJECTED DOSE (153Sm) IN VARIOUS TISSUES

| Tissue | S.C.[d] | I.M.[d] | I.V.[d] |
|---|---|---|---|
| Skeleton[a] | 49 | 145 | 50 |
| Liver | 0.14 | 0.35 | 0.14 |
| Kidney | 0.32 | 0.32 | 0.36 |
| Spleen | 0.006 | 0.005 | 0.001 |
| Muscle[b] | 0.40 | 0.053 | 0.22 |
| Blood[c] | 0.45 | 0.35 | 0.12 |

[a]was derived by multiplying the % in the femur by 25
[b]was estimated as 43% of body weight
[c]was estimated at 6.5% of body weight.
[d]average of 2 rats The results from Table 7 indicate that the biodistribution is similar regardless of the mode of administration.

EXAMPLE 10

Five 3 mL EDTMP kits, prepared by the procedure of Example 4, were reconstituted with the solutions shown in the Table 8 and the pH measured.

TABLE 8

ACID CONCENTRATIONS

| [Ca] M | [HCl] M | pH |
|---|---|---|
| 0.0375 | 0.087 | 7.42 ± 0.03 |
| 0.060 | 0.072 | 7.40 ± 0.06 |
| 0.070 | 0.065 | 7.39 ± 0.05 |

Solutions containing about 1 mCi/mL of $^{153}$Sm and a total Sm concentration of $3\times10^{-4}$M with the Ca content shown in the above Table for each sample and the complex yield determined to be >99% for each sample.

The Ca containing acid solutions describer in Table 12 were used to titrate existing 3.0 mL EDTMP kits to study the effect of the volume of solution used for reconstitution on final pH. Two mL of each solution was added to each kit and the pH measured. Another 2.0 mL was added in 200 µL aiquots with pH measurements taken after each addition. The results showed that for all of the solutions up to 3.6 mL can be added to a 3.0 mL kit without falling below pH 7.0.

The effect of the added Ca on osmolality of the reconstituted kits was determined. The solutions form Table 12 were used to reconstitute 3.0 mL kits of EDTMP. Following reconstitution, the pH of the solution was measured and the osmolality determined by freezing point depression. The results are shown in Table 9.

TABLE 9

EFFECT OF ADDED CALCIUM ON SOLUTION MOLALITY

| [Ca] | [HCl] | pH | Molality | % of Isotonic |
|---|---|---|---|---|
| 0 | 0.11 | 7.50 | 0.491 | 164 |
| 0.0375 | 0.087 | 7.40 | 0.558 | 186 |
| 0.060 | 0.072 | 7.35 | 0.595 | 198 |
| 0.070 | 0.065 | 7.35 | 0.606 | 202 |

The data form Table 9 demonstrates that the kits as formulated are hypertonic and that adding Ca to the radionuclide solutions used to reconstitute to kits only slightly increases the hypertonic result. In a discussion of the influence of formulation on the route of administration of drugs it is known that with intravenous solutions isotonicity becomes less important as long as administration is slow enough to permit dilution or adjustment in the blood [see, for example, P. P. DeLuca and J. C. Boylan, "Formulation of Small Volume Parenterals in Pharmaceutical Dosage Forms", Parenteral Medications Vol. 1, pg. 140, eds. K. E. Avis, L. Lachman, and H. A. Lieberman, pub. Marcel Dekker Inc., N.Y. (1984)].

EXAMPLE 11

Method D

To test the acute effects of $^{153}$Sm-Na-EDTMP and $^{153}$Sm-(Ca/Na)-EDTMP upon heart rate and pulse and serum calcium levels shortly after I.V. injection to Beagle dogs the following experiment was preformed. The effects of the rate of infusion were also measured.

The $^{153}$Sm-Na-EDTMP, Sample VIII, was prepared from 630 mg of EDTMP and 414 mg NaOH that was lyophilized and sterilized and then reconstituted with sterile Sm, $3\times10^{-4}$M in 0.1M HCl.

The $^{153}$Sm-(Ca/Na)-EDTMP, Sample IX, was prepared from 630 mg of EDTMP, 245 mg NaOH and 95 mg Ca(OH)$_2$ that was lyophilized and sterilized and then reconstituted with sterile Sm, $3\times10^{-4}$M in 0.01M HCl.

Each complex used for injection was prepared by adding 18.0 mL of the Sm solution to respective lyophilized EDTMP formulation. The final concentration for the formulation was 35 mg/mL of the Sm-EDTMP complex. The formulations were used within 15 min of preparing with the remaining solution frozen for analysis. Analysis of the formulations used for injection confirmed that the injections were at the targeted concentrations.

Young adult male Beagle dogs, approximately 33 weeks of age and weighing from 8.1 to 10.9 kg were used. The dogs were given a complete physical examination by a veterinarian, allowed to acclimate to the laboratory environment for least 30 days, revaccinated against distemper, adenovirus type 2 hepatitis, parainfluenza and parvovirus using Adenoimmune™-7-L (made by Tech America, Biologics Corp.). The dogs were individually identified by a unique number tattooed in the ear by the supplier. The dogs were maintained under the procedures established by the American Association for the Accreditation of Laboratory Animal Care. The laboratory used for the tests is accredited.

A single fasted male dog, selected at random, was given a I.V. dose of 30 mg/kg body weight of of either Sample VII or IX via a catheter inserted into the cephalic vein. The injection site was shaved and prepared with antiseptic solution prior to catheterization. The injection was given at the rate of about 2.0 mL/min (70 mg/min) such that the injection took about four min.

Two additional male Beagle dogs were given the same dose level of either Sample VII or IX as rapidly as possible, about 15 mL/min. The methods of infusions were as before. This was done about 2 weeks after the first injection to verify the previously reported results regarding rate of infusion.

Blood samples were obtained from the jugular vein for analysis of serum calcium and total protein immediately prior to injection and following completion of injection and also at about 5, 15, 30 and 45 min and 1, 2 and 4 hrs post-injection. The ventral neck was shaved and prepared with antiseptic solution as above. The dog was monitored for clinical effects during this time period and heart rate and pulse were recorded at each of these time points.

As only individual dogs comprised each of these treatment regimens, summary tables seems inappropriate. However, the slow I.V. injections of 2.0 mL/min (70 mg/mL) of 30 mg/kg of body weight of either Sample VIII or IX did not produce any clinical signs. The heart rate increased 7 to 10% for each of the formulations; however, this result was considered merely to represent a response to excitement as canine heart rate can vary markedly in response to environmental stimuli. Although there were minimal changes in serum total calcium, the changes are difficult to ascribe to treatment.

When the rate of injection was increased to as fast as was practicable (about 15 mL/min), clinical signs were noted with each of the Samples. Involuntary muscular movements, primarily fine tremors of all muscles, with increased respiration and whining were noted for the dog receiving Sample VIII. These effects were first noted about 20 seconds after injection began and lasted about 2 min. The dog appeared normal by about 5 min post-injection. The heart rate increased by >50% during this same time period. Serum total calcium levels were decreased during this time period; however, this decrease was relatively minor and was accompanied by similar changes in serum total protein. It was impossible to ascribe any definitive effects on total calcium due to injection.

Although the dog receiving Sample IX also showed clinical signs, it is uncertain as to whether these were involuntary movements, as the movements were characteristic of resistance to restraint, as appeared to be the case for the dog that received Sample VIII. The period of increased activity by the dog lasted only about 30 sec and the dog appeared normal by about 100 sec post-injection. The heart rate was only increased about 13%. Serum calcium levels were increased during the post-injection period, but concomitant changes in total protein make this result difficult to interpret.

In summary, dogs receiving 30 mg/kg of either Sample VIII or IX by slow I.V. injection had no effects attributable to the injection. When the injection was given by rapid bolus injection, clinical signs were noted for each sample. The effects were more pronounced with Sample VIII than Sample IX.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A radiopharmaceutical formulation consisting essentially of a complex of a radionuclide of Samarium-153, Holmium-166, Ytterbium-175, Lutetium-177, or Gadolinimum-159 with a ligand of ethylenediaminetetramethylenephosphonic acid, diethylenetriaminepentamethylenephosphonic acid, hydroxyethylethyenediaminetrimethylenephosphonic acid, nitrilotrimethylenephosphonic acid, tris(2-aminoethyl)aminehexamethylenephosphonic acid, 1-carboxyethylenediaminetetramethylenephosphonic acid or bis(aminoethylpiperazine)tetramethylenephosphonic acid, or physiologically-acceptable salts thereof, which is frozen at a temperature of from about minus 77° to about minus 196° C., and then thawed prior to use without obtention of the formation of significant radiolytic degradation by-products after about six hours or more from the time of formation of said complex.

2. A radiopharmaceutical formulation of claim 1 wherein the radionuclide is Samarium-153 or Holmium-166.

3. A radiopharmaceutical formulation of claim 2 wherein the radionuclide is Samarium-153.

4. A radiopharmaceutical formulation of claim 1 wherein the ligand is ethylenediaminetetramethylenephosphonic acid, diethylenetriaminepentamethylenephosphonic acid, hydroxyethylethylenediaminetrimethylenephosphonic acid, tris(2-aminoethyl)aminehexamethylenephosphonic acid, 1-carboxyethylenediaminetetramethylenephosphonic acid, or bis(aminoethylpiperazine)tetramethylenephosphonic acid, or physiologically-acceptable salts thereof.

5. A radiopharmaceutical formulation of claim 4 wherein the ligand is ethylenediaminetetramethylenephosphonic acid, or physiologically-acceptable salts thereof.

6. A radiopharmaceutical formulation of claim 1 comprising $^{153}$samarium-ethylenediaminetetramethylenephosphonic acid, or physiologically-acceptable salts thereof.

7. A radiopharmaceutical formulation of claim 1 comprising $^{166}$holmium-ethylenediaminetetramethylenephosphonic acid, or physiologically-acceptable salts thereof.

8. A radiopharmaceutical formulation of claim 1 wherein the freezing was done using liquid nitrogen at a temperature of about minus 196° C.

9. A radiopharmaceutical formulation of claim 1 wherein the freezing was done using dry ice at a temperature of about minus 78° C.

10. A radiopharmaceutical formulation of claim 1 wherein the freezing was done using acetone-dry ice at a temperature of about minus 77° C.

11. A radiopharmaceutical formulation of claim 1 wherein a divalent metal is added prior to freezing.

12. A radiopharmaceutical formulation of claim 11 wherein the divalent metal is $Fe^{+2}$, $Mn^{+2}$ or an alkaline earth metal ion.

13. A radiopharmaceutical formulation of claim 12 wherein the alkaline earth metal ion is $Be^{+2}$, $Mg^{+2}$, $Ca^{+2}$, $Sr^{+2}$ or $Ba^{+2}$.

14. A radiopharmaceutical formulation of claim 13 wherein the alkaline earth ion is $Ca^{+2}$.

15. A radiopharmaceutical formulation of claim 11 wherein the molar ratio of divalent metal to ethylenediaminetetramethylenephosphonic acid is from about 0.25 to about 1.

16. A radiopharmaceutical formulation of claim 15 wherein the molar ratio of divalent metal to ethylenediaminetetramethylenephosphonic acid is from about 0.5 to about 1.

17. A radiopharmaceutical formulation of claim 16 wherein the molar ratio of divalent metal to ethylenediaminetetramethylenephosphonic acid is from about 0.75 to about 1.

18. A radiopharmaceutical formulation of claim 17 wherein the molar ratio of divalent metal to ethylenediaminetetramethylenephosphonic acid is from about 0.9 to about 1.

19. A radiopharmaceutical formulation of claim 14 wherein the molar ratio of $Ca^{+2}$ to ethylenediaminetetramethylenephosphonic acid is from about 0.9 to about 1.

20. A method of administering a radiopharmaceutical formulation which comprises a complex of a radionuclide of Samarium-153, Holmium-166, Ytterbium-175, Lutetium-177, or Gadolinium-159 with a ligand of ethylenediaminetetramethylenephosphonic acid, diethylenetriaminepentamethylenephosphonic acid, hydroxyethylethylenediaminetrimethylenephosphonic acid, nitrilotrimethylenephosphonic acid, tris(2-aminoethyl)aminehexamethylenephosphonic acid, 1-carboxyethylenediaminetetramethylenephosphonic acid, or bis(aminoethylpiperazine)tetramethylenephosphonic acid, or physiologically-acceptable salts thereof, which method comprises (1) preparing said complex, (2) freezing said complex at a temperature of from about minus 77° to about minus 196° C., (3) thawing said complex, and (4) administering said complex to a patient intravenously, intraperitoneally, intramuscularly or subcutaneously.

21. A method of administering a radiopharmaceutical formulation which comprises a complex of a radionuclide of Samarium-153, Holmium-166, Ytterbium-175, Lutetium-177, or Gadolinium-159 with a ligand of ethylenediaminetetramethylenephosphonic acid, or physiologically-acceptable salts thereof, and a $Ca^{+2}$ ion wherein the molar ratio of $Ca^{+2}$ to ethylenediaminetetramethylenephosphonic acid is from about 0.9 to about 1, which method comprises (1) preparing said complex, (2) freezing said complex at a temperature of from about minus 77° to about minus 196° C., (3) thawing said complex, and (4) administering said complex to a patient intravenously, intraperitoneally, intramuscularly or subcutaneously.

22. A method for administering a radiopharmaceutical formulation to a patient which comprises a complex which contains $^{153}$samarium-ethylenediaminetetramethylenephosphonic acid, which method comprises (1) preparing said complex, (2) freezing said complex at a temperature of from about minus 77° to about minus 196° C., (3) thawing said complex, and (4) administering said complex to a patient intravenously, intraperitoneally, intramuscularly or subcutaneously.

23. A method for administering a radiopharmaceutical formulation to a patient which comprises a complex which contains $^{153}$samarium-ethylenediaminetetramethylenephosphonic acid, having $Ca^{+2}$ present, which method comprises (1) preparing said complex, (2) freezing said complex at a temperature of from about minus 77° to about minus 196° C., (3) thawing said complex, and (4) administering said complex to a patient intravenously, intraperitoneally, intramuscularly or subcutaneously.

24. A radiopharmaceutical formulation consisting essentially of a complex of a radionuclide of Samarium-153, Holmium-166, Ytterbium-175, Lutetium-177, or Gadolinimum-159 with a ligand of ethylenediaminetetramethylenephosphonic acid, diethylenetriaminepentamethylenephosphonic acid, hydroxyethylethyenediaminetrimethylenephosphonic acid, nitrilotrimethylenephosphonic acid, tris(2-aminoethyl)aminehexamethylenephosphonic acid, 1-carboxyethylenediaminetetramethylenephosphonic acid or bis(aminoethylpiperazine)tetramethylenephosphonic acid, or physiologically-acceptable salts thereof, which is frozen at a temperature of from about minus 77° to about minus 196° C.

25. A radiopharmaceutical formulation of claim 24 wherein the radionuclide is Samarium-153 or Holmium-166.

26. A radiopharmaceutical formulation of claim 25 wherein the radionuclide is Samarium-153.

27. A radiopharmaceutical formulation of claim 24 wherein the ligand is ethylenediaminetetramethylenephosphonic acid, or physiologically-acceptable salts thereof.

28. A radiopharmaceutical formulation of claim 24 comprising $^{153}$samarium-ethylenediaminetetramethylenephosphonic acid, or physiologically-acceptable salts thereof.

29. A radiopharmaceutical formulation of claim 24 comprising $^{166}$holmium-ethylenediaminetetramethylenephosphonic acid, or physiologically-acceptable salts thereof.

30. A radiopharmaceutical formulation of claim 24 wherein a divalent metal is added prior to freezing.

31. A radiopharmaceutical formulation of claim 30 wherein the divalent metal is $Fe^{+2}$, $Mn^{+2}$ or an alkaline earth metal ion.

32. A radiopharmaceutical formulation of claim 31 wherein the alkaline earth metal ion is $Be^{+2}$, $Mg^{+2}$, $Ca^{+2}$, $Sr^{+2}$ or $Ba^{+2}$.

33. A radiopharmaceutical formulation of claim 32 wherein the alkaline earth ion is $Ca^{+2}$.

34. A radiopharmaceutical formulation of claim 30 wherein the molar ratio of divalent metal to the ligand ethylenediaminetetramethylenephosphonic acid is from about 0.25 to about 1.

35. A method for preparing a radiopharmaceutical formulation comprising a complex of a radionuclide of Samarium-153, Holmium-166, Ytterbium-175, Lutetium-177, or Gadolinium-159 with a ligand of ethylenediaminetetramethylenephosphonic acid, diethylenetriaminepentamethylenephosphonic acid, hydroxyethylethylenediaminetrimethylenephosphonic acid, nitrilotrimethylenephosphonic acid, tris(2-aminoethyl)aminehexamethylenephosphonic acid, 1-carboxyethylenediaminetetramethylenephosphonic acid, or bis(aminoethylpiperazine)tetramethylenephosphonic acid, or physiologically-acceptable salts thereof, which method comprises (1) preparing said complex, (2) freezing said complex at a temperature of from about minus 77° to about minus 196° C., and (3) thawing said complex.

36. A method of claim 35 for preparing a radiopharmaceutical formulation comprising as the complex $^{153}$samarium-ethylenediaminetetramethylenephosphonic acid.

37. A method for preparing a radiopharmaceutical formulation comprising a complex of a radionuclide of Samarium-153, Holmium-166, Ytterbium-175, Lutetium-177, or Gadolinium-159 with a ligand of ethylenediaminetetramethylenephosphonic acid, or physiologically-acceptable salts thereof, and a $Ca^{+2}$ ion wherein the molar ratio of $Ca^{+2}$ to ethylenediaminetetramethylenephosphonic acid is from about 0.9 to about 1, which method comprises (1) preparing said complex, (2) freezing said complex at a temperature of from about minus 77° to about minus 196° C., and (3) thawing said complex.

38. A method of claim 37 for preparing a radiopharmaceutical formulation comprising as the complex $^{153}$samarium-ethylenediaminetetramethylenephosphonic acid.

* * * * *